United States Patent [19]
Bryan et al.

[11] Patent Number: 4,695,534

[45] Date of Patent: Sep. 22, 1987

[54] SILVER HALIDE PHOTOSENSITIVE MATERIAL

[75] Inventors: Philip S. Bryan; Arthur H. Herz, both of Rochester, N.Y.

[73] Assignee: Eastman Kodak Company, Rochester, N.Y.

[21] Appl. No.: 947,452

[22] Filed: Dec. 29, 1986

[51] Int. Cl.[4] .................... G03C 1/08

[52] U.S. Cl. .................... 430/569; 430/600; 430/603

[58] Field of Search .................... 430/251, 455, 569, 600, 430/603, 611

[56] References Cited

U.S. PATENT DOCUMENTS 3,021,215 2/1962 Williams et al. .................... 430/603

FOREIGN PATENT DOCUMENTS 85420 7/1978 Japan .................... 430/603

*Primary Examiner*—Richard L. Schilling
*Assistant Examiner*—Patrick Doody
*Attorney, Agent, or Firm*—Thomas F. Kirchoff

[57] ABSTRACT

A photographic silver halide emulsion comprising a thioether substituted pyridine compound having improved ripening properties. A process for preparation of the emulsion is also described.

20 Claims, No Drawings

SILVER HALIDE PHOTOSENSITIVE MATERIAL

The present invention relates to a silver halide photosensitive emulsion and to a process for preparation thereof. In particular, this invention relates to a silver halide emulsion comprising one or more thioether substituted compounds.

Thioether compounds are recognized as having a variety of uses in photography, including uses as ripening and sensitizing agents for silver halide grains. For example, Japanese Patent Publication No. 85420/1978 (priority of Jan. 6, 1977) discloses thioether compounds which are stated to be capable of enhancing the sensitivity and growth rate of photographic silver halide grains without causing undesirable increases in fog formation during storage prior to use. The described thioether compounds comprise terminal carboxy groups on alkyl thioether chains bonded to a benzene nucleus. However, as is shown below by comparative data, the thioether compounds of this Patent Publication fail to impart the growth enhancement and fog reduction which can be obtained with compounds of this invention.

U.S. Pat. No. 3,021,215 describes long chain polythiaalkylenediol compounds as being useful sensitizing agents for silver halide. These compounds contain sulfur atoms which are separated from each other by alkylene groups. However, the described compounds do not provide sufficient ripening properties and, as shown below by comparative data, cause unacceptably high levels of fog formation during storage prior to use.

Accordingly, the objects of the present invention are to provide a photographic silver halide emulsion, and a process for preparation thereof, which emulsion comprises a compound which improves silver halide crystal growth rates and which imparts superior ripening properties without causing fog formation upon extended storage thereof.

The present invention provides a photographic silver halide emulsion which comprises a thioether substituted pyridine compound having the structural formula:

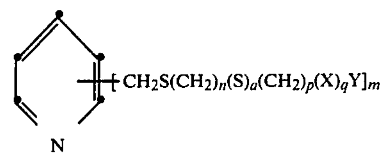

wherein

X is $-NHCO(CH_2)_n$;

Y is hydrogen, hydroxyl or a carboxylic group of the formula —COOR′, where R′ is hydrogen or an alkyl group having from 1 to about 5 carbon atoms;

a is 0 or 1;

n is 1 or 2;

p and q are each 0, 1 or 2; and m is from 2 to 5, or a quaternary ammonium salt thereof.

Preferred pyridine compounds useful in this invention include those where the thioether substituents are present in the 2 and 6 positions of the pyridine ring. Moreoever, while "m" in the above formula can be an integer of from 2 to 5, it is preferred to utilize a pyridine compound where m is 2 since such compounds provide good results and are more economical to manufacture. Most preferred compounds include those where the substituents have terminal hydroxy (OH) or carboxy (COOH) groups.

With respect to formation of an acid salt of a substituted pyridine compound as described herein, this can readily be accomplished by reacting, for example, an inorganic acid or a monocarboxylic acid with the pyridine compound. Typical reactants include hydrochloric acid and acetic acid.

It is also possible to form alkali metal or ammonium salts with terminal carboxy groups on compounds described herein.

Specific examples of thioether compounds falling within the description of the invention include:

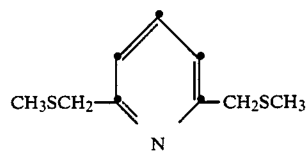

1.

$HO(CH_2)_2SCH_2$— [pyridine] —$CH_2S(CH_2)_2OH$

2.

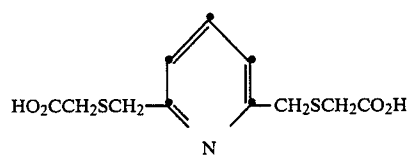

3.

$CH_3O_2CCH_2SCH_2$— [pyridine] —$CH_2SCH_2CO_2CH_3$

4.

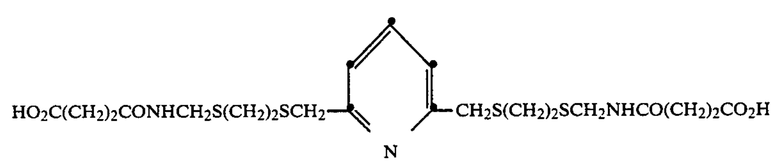

5.

-continued

6.

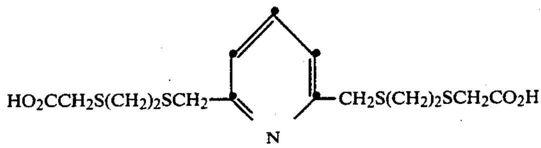

7.

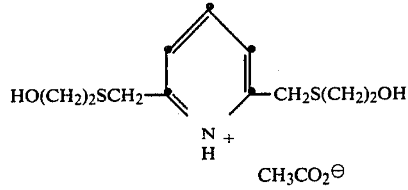

The thioether substituted pyridine compounds described herein can be synthesized by the reaction of a thiol with a bis(haloalkyl)pyridine in base. The following synthesis of Compound 2 is presented as a particular illustration of a synthetic route which can be used to obtain the compounds disclosed herein.

Synthesis I—Preparation of Compound 2

To 9.8 g (0.125 mole) of 2-mercaptoethanol in 25 ml of methanol was added 250 ml of 0.5M sodium methoxide in methanol. The addition of 10 g (0.057 mole) of bis-2,6-(chloromethyl)pyridine [J. Chem. Soc., 3594 (1958)] yielded a clear solution which deposited a white solid while it was heated at reflux under nitrogen for 4 days. The solvent was removed in vacuo and the resulting oil and salt mixture was dissolved in 100 ml water. This aqueous solution was extracted twice using 75 ml portions of chloroform. The combined extracts were washed with water, dried over $MgSO_4$, and treated with decolorizing charcoal. Solvent removal yielded an oil which was chromatographed using silica gel. The impurities were eluted with diethyl ether and the product was removed with methanol. After the methanol was removed, the oil was dissolved in methylene chloride and the solution was dried and treated with charcoal. Solvent removal gave a pale yellow oil; yield 13.5 g (91%).

This invention also provides a process for preparation of a silver halide emulsion which comprises adding from about 0.001 to about 10 g of a thioether compound, as described above, to said emulsion during preparation thereof or prior to coating the emulsion on a support.

In the present invention the described thioether compounds may be added to the silver halide emulsion at various stages during manufacture. They may be added singly or in combination with other ripening agents, including other thioether compounds or their silver complexes. For example, the compounds may be added during formation of silver halide grains, during the physical or chemical ripening stage, or in a separate step before coating. The silver halide grains can be formed according to processes generally well known in the art, with a double jet type process being preferred.

The double jet process comprises adding a silver nitrate aqueous solution and an aqueous solution of one or more halides (e.g., an alkali metal halide such as potassium bromide) simultaneously to a stirred solution of silver halide-protecting colloid (e.g., gelatin or gelatin derivative) through two separate jets. A thioether compound as described herein is preferably added to the protective colloid solution before initiation of silver halide formation.

Conditions for forming silver halide grains such as pH, pAg, temperature, etc., are not particularly limited when employed using compounds described herein. The pH is generally about 1 to 9, preferably about 2 to 6, and pAg is generally about 5 to 11, preferably about 7.0 to 10.0. Silver halide grains may be formed at temperatures between about 30° to about 90° C., with about 35° C. to about 80° C. being preferred.

An organic thioether compound as described herein is preferably added during precipitation of silver halide grains and/or during physical ripening in an amount of from about 0.001 to 10 g, preferably about 0.01 to 1 g, per mol of silver halide.

When an acid-substituted thioether compound of the type disclosed herein remains in a silver halide emulsion following preparation thereof, a reduction in fog formation upon extended storage is often obtained. An effective concentration to retard such fog formation is from about $10^{-6}$ to about $0.5\times10^{-2}$ mol of the compound per mol of silver halide.

Gelatin is preferred as the binder or protective colloid for the photographic emulsion of the present invention. However, other hydrophilic colloids are also suitable. For example, proteins such as gelatin derivatives, graft polymers of gelatin and other polymers, albumin, casein, cellulose derivatives such as hydroxyethyl cellulose, carboxymethyl cellulose, cellulose, sulfate, sugar derivatives such as sodium alginate, starch derivatives and various synthetic hydrophilic homopolymers or copolymers such as polyvinyl alcohol, poly-N-vinylpyrrolidone, polyacrylic acid, polymethacrylic acid, polyacrylamide, polyvinylimidazole, polyvinyl pyrazole can be used.

Acid-processed gelatin can be used as well as lime-processed gelatin. Further, gelatin hydrolyzates, and enzyme-hydrolyzed products of gelatin are also usable.

Surface active agents may be incorporated in a photographic emulsion layer or in another hydrophilic colloid layer as a coating aid to prevent build-up of static charge, to improve lubrication properties, to improve emulsion dispersion, to prevent adhesion, and to improve such photographic characteristics as acceleration of development, increase in contrast, or sensitization.

A photographic emulsion of the present invention can be applied to many different silver halide photographic light-sensitive materials due to its high photographic sensitivity, contrast, and fog reduction. For example, it can be used in high speed black-and-white negative films, in X-ray films and in multilayer color negative films.

A photographic emulsion of the present invention may contain antifogging agents or emulsion stabilizing agents, such as for example azaindenes, thionamides, azoles and the like.

The photographic emulsion of the present invention may be spectrally sensitized with dyes. Dyes which can be used include cyanine dyes, merocyanine dyes, composite cyanine dyes, composite merocyanine dyes, and hemioxonol dyes. Particularly useful dyes are those belonging to the merocyanine class. These dyes contain as a basic heterocyclic ring nucleus any nucleus ordinarily used in cyanine dyes.

The photographic emulsion of the present invention may contain color image-forming couplers, i.e., compounds capable of reacting with an oxidation product of an aromatic amine (usually a primary amine) to form a dye. Non-diffusing couplers containing a ballast group are desirable. Either 4-equivalent and 2-equivalent couplers are usable. In addition, colored couplers showing the effect of color correction, or couplers releasing a development inhibitor upon development (so-called DIR couplers) may be used.

A photographic emulsion of the present invention is coated on a support conventionally used for photographic light-sensitive materials such as a flexible support (e.g., plastic film, paper, etc.) or a rigid support (e.g., glass, etc.) according to a dip-coating method, roller coating method curtain coating method or extrusion coating method.

Emulsions of the present invention can be applied to a multilayer multicolor photographic material comprising a support having provided thereon at least two layers having different spectral sensitivities. Multilayer multicolor photographic materials usually comprise a support having provided thereon at least one red-sensitive emulsion layer, at least one green-sensitive emulsion layer, and at least one blue-sensitive emulsion layer. The order of these layers can optionally be selected as occasion demands. Usually, a cyan-forming coupler is associated with the red-sensitive emulsion layer, a magenta-forming coupler is associated with the green-sensitive emulsion layer, and a yellow-forming coupler is associated with the blue-sensitive emulsion layer. In some cases, however, different layer arrangements may be employed.

The photographic emulsions obtained by the present invention can be processed according to known methods. A developer to be used for the black-and-white processing can contain conventional developing agents such as dihydroxybenzenes (e.g., 1-phenyl-3-pyrazolidone), aminophenols (e.g., N-methyl-p-aminophenol), 1-phenyl-3-pyrazolines or ascorbic acids.

As color-developing agent, there can be used primary aromatic amine developing agents such as phenylenediamines (e.g., 4-amino-N,N-diethylaniline, 3-methyl-4-amino-N,N-diethylaniline, 4-amino-4-ethyl-N-hydroxyethylaniline, 3-methyl-4-amino-N-ethyl-N-hydroxyethylaniline, 3-methyl-4-amino-N-ethyl-N-methanesulfonamidoethylaniline and 4-amino-3-methyl-N-ethyl-N-methoxyethylaniline. In addition, the developing agents described in L. F. A. Mason, Photographic Processing Chemistry (Focal Press, 1966), pp. 226–229, as well as those described in U.S. Pat. Nos. 2,193,015 and 2,592,364 may be used.

The invention is described in further detail by the following non-limiting examples.

EXAMPLE I

The ripening activity of compounds of this invention compared with prior art compounds was determined from Rayleigh light scatter measurements of dispersed silver halides (L. Oppenheimer, T. H. James and A. H. Herz in "Particle Growth in Suspensions". A. L. Smith, Editor, Academic Press, London, 1973, pp. 159–178).

Tests for silver halide growth rates were carried out with about 1 mM of AgBr suspended in 0.1% gelatin (isoionic point 4.9), 30 vol. % methanol, at pBr 3, pH 3, 40° C. Additive concentrations were 0.2 mmol per liter AgBr suspension. Turbidity was determined as a function of time. A linear plot (slope rate), thus obtained, was taken as a measure of AgBr growth (or ripening) rate. Results are recorded below in Table I.

TABLE I

| Compound | AgBr Growth Rate |
|---|---|
| none (control) | 1.0 |
| A (prior art) | 1.0 |
| B (prior art) | 2.1 |
| 2 (invention) | 3.2 |

Compound A is 2,5-dithiosuberic acid ($(-CH_2SCH_2COOH)_2$ and is disclosed as Compound 7 in Japanese Patent Publication No. 85420/1978. Compound B is 3,6-dithia-1,8-octanediol which is disclosed in U.S. Pat. No. 3,021,215.

Table I shows thioether substituted pyridine Compound No. 2 of this invention to be appreciably more active as a silver halide ripening agent than the compounds of the prior art.

EXAMPLE 2

When the thioether moiety also comprises an acid substituent, the pyridine compound as described herein can be incorporated in a chemically sensitized high speed silver halide emulsion were less fog is caused as compared with known thioether ripening agents. This is demonstrated below.

The compounds indicated in the following Table were added at concentrations of 1 mmol/mol Ag and at 40° C., to sulfur and gold-sensitized negative AgBrI gelatin emulsions containing about 0.001M KBr at about pH 6. The emulsions were coated and processed in a hydroquinone/monomethyl-p-aminophenol sulfate developer such as those commercially available under the tradenames Kodak Developer DK-50 and D-19. Sensitivity values were normalized with respect to a control (100). Accelerated aging tests were carried out by storing coatings for 1 week at 49° C./50% relative humidity (RH). Results are recorded in TABLE II.

TABLE II

| Compound | Relative Speed | Fog | |
|---|---|---|---|
| | | Fresh | After Storage |
| none (control) | 100 | 0.10 | 0.50 |
| B(*) (prior art) | 100 | 0.19 | 1.45 |
| 5 (invention) | 105 | 0.11 | 0.16 |

(*)Compound B is identified above in Example 1.

From the results reported in Table II it is seen that appreciable fog reduction is achieved with a thioether substituted pyridine compound as described herein when compared with two prior art compound and also that the fog reduction is realized without loss of photographic speed.

While the above examples illustrate use of this invention with respect to silver bromide in excess bromide ion, the invention is also applicable to other silver halide compositions including AgClI and AgClBr, as well as silver chloride dispersions containing excess chloride ion and silver iodide dispersions containing excess iodide ion.

The thioether compounds described herein have also been found to form silver complexes that do not yield sulfide ions which cause adverse sensitometric changes. These thioether compounds are active silver halide solvents and are capable of dissolving silver halide in aqueous dispersions, for example in silver salt diffusion transfer systems.

This invention has been described in detail with particular reference to preferred embodiments thereof, but it will be understood that variations and modifications can be effected within the spirit and scope of the invention.

What is claimed is:

1. A silver halide photographic emulsion comprising a thioether substituted compound having the structural formula:

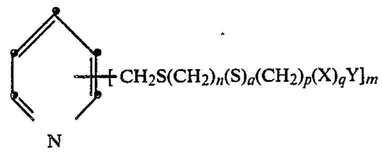

where

X is $NHCO(CH_2)_n$;

Y is hydrogen, hydroxyl or a carboxylic group of the formula COOR' where R' is hydrogen or an alkyl group having from 1 to about 5 carbon atoms;

a is 0 or 1;

n is 1 or 2;

p and q are each 0, 1 or 2; and m is from 2 to 5, or a quaternary ammonium salt thereof.

2. The photographic emulsion of claim 1 wherein m is 2.

3. The photographic emulsion of claim 2 wherein said thioether substituent is present in each of the 2 and 6 positions of the pyridine ring.

4. The photographic emulsion of claim 3 wherein said thioether substituents have terminal hydroxy or carboxy groups.

5. The photographic emulsion of claim 1 wherein the compound is present in an amount of from about 0.001 to about 10 g thereof per mol of silver halide.

6. The photographic emulsion of claim 5 wherein the compound is present in an amount of from about 0.01 to about 1 g thereof per mol of silver halide.

7. The photographic emulsion of claim 1 wherein the compound is present in an amount of from about $10^{-6}$ to about $0.5\times10^{-2}$ mol thereof per mol of silver halide.

8. The photographic emulsion of claim 1 wherein said compound has the structural formula:

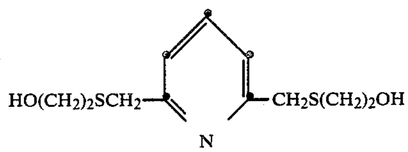

9. The photographic emulsion of claim 1 wherein said compound has the structural formula:

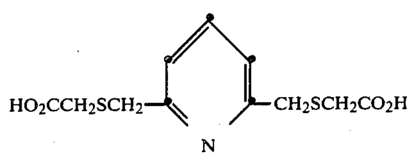

10. The photographic emulsion of claim 1 wherein said compound has the structural formula:

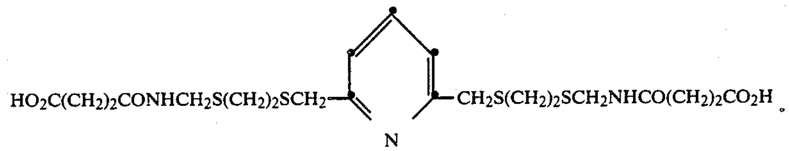

11. The photographic emulsion of claim 1 wherein said compound has the structural formula:

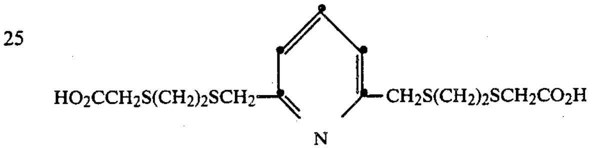

12. The photographic emulsion of claim 1 wherein said compound has the structural formula:

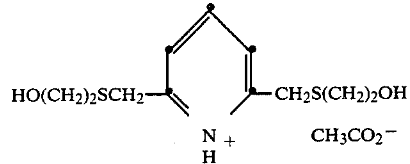

13. In a process for the preparation of a silver halide emulsion, the improvement which comprises adding, during preparation of said emulsion or prior to coating thereof on a support, from about 0.001 to about 10 g per mol of silver halide of a compound having the structural formula:

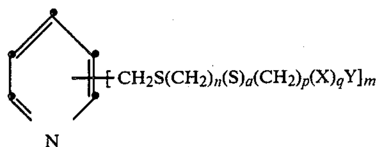

where

X is $NHCO(CH_2)_n$;

Y is hydrogen, hydroxyl or a carboxylic group of the formula COOR' where R' is hydrogen or an alkyl group having from 1 to about 5 carbon atoms;

a is 0 or 1;

n is 1 or 2;

p and q are each 0, 1 or 2; and m is from 2 to 5, or a quaternary ammonium salt thereof.

14. The process of claim 13 wherein said pyridine compound has thioether substituents in each of the 2 and 6 positions thereof.

15. The process of claim 14 wherein said substituents have terminal hydroxy or carboxy groups.

16. The process of claim 13 wherein said compound is added during silver halide formation or during ripening.

17. The process of claim 13 wherein the compound is added in an amount of from about 0.01 to about 1 g thereof per mol of silver halide.

18. The process of claim 13 wherein the compound has the structural formula:

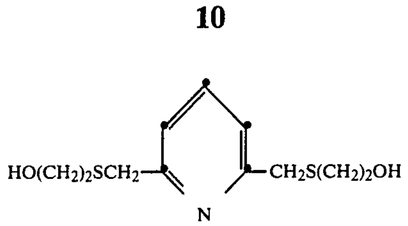

19. The process of claim 13 wherein the compound has the structural formula:

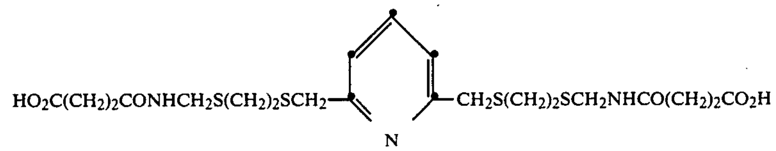

20. A silver halide emulsion prepared by the process of claims 13, 14, 15, 16, 17, 18 or 19.

* * * * *